United States Patent
Lo

(10) Patent No.: US 6,402,721 B1
(45) Date of Patent: Jun. 11, 2002

(54) SAFETY HYPODERMIC SYRINGE WITH DETACHABLE PLUNGER

(76) Inventor: Cheng-Chi Lo, 2F, No. 77, Ming-Sheng Rd., Yungho City, Taipei Hsien (TW)

(*) Notice: Subject to any disclaimer, the term of this patent is extended or adjusted under 35 U.S.C. 154(b) by 44 days.

(21) Appl. No.: 09/709,469

(22) Filed: Nov. 13, 2000

(30) Foreign Application Priority Data

Jun. 30, 2000 (TW) .................................... 89211319 U

(51) Int. Cl.⁷ .............................................. A61M 5/00
(52) U.S. Cl. ...................................... 604/110; 604/195
(58) Field of Search ............................... 604/110, 192, 604/195, 198, 218, 240, 241, 242; 128/919

(56) References Cited

U.S. PATENT DOCUMENTS

| | | | | |
|---|---|---|---|---|
| 5,346,474 A | * | 9/1994 | King | 604/110 |
| 5,395,346 A | * | 3/1995 | Maggioni | 604/195 |
| 5,405,327 A | * | 4/1995 | Chen | 604/195 |
| 5,531,705 A | * | 7/1996 | Alter et al. | 604/195 |
| 5,575,774 A | * | 11/1996 | Chen | 604/110 |
| 6,193,687 B1 | * | 2/2001 | Lo | 604/110 |

* cited by examiner

Primary Examiner—Anhtuan T. Nguyen
(74) Attorney, Agent, or Firm—Bacon & Thomas, PLLC

(57) ABSTRACT

A safety hypodermic syringe is so designed that the needle assembly can be moved with the plunger assembly and received inside the barrel after the service of the syringe, and the plunger can be disconnected from the stopper and removed from the barrel for recycling. The barrel has an inside annular flange defining a plane not perpendicular to the axis of the barrel, so that the plunger is tilted in one direction after pulled to the back side of the barrel, preventing the stopper holder and the stopper from being pulled out of the barrel, and enabling the plunger to be easily disconnected from the stopper holder.

6 Claims, 3 Drawing Sheets

SAFETY HYPODERMIC SYRINGE WITH DETACHABLE PLUNGER

BACKGROUND OF THE INVENTION

The present invention relates to a safety hypodermic syringe, and more particularly to such a safety hypodermic syringe, which has a detachable plunger that can be disconnected from the syringe barrel after the service of the syringe.

Various functional safety hypodermic syringes have been well known. These safety hypodermic syringes are made for enabling the user to pull the needle assembly backwards to the inside of the syringe barrel after injection, preventing possible contamination. However, all parts of conventional safety hypodermic syringes must be thrown away after their use, i.e., neither part of used safety hypodermic syringes can be recycled.

SUMMARY OF THE INVENTION

The invention has been accomplished under the circumstances in view. It is the main object of the present invention to provide a safety hypodermic syringe, which enables the plunger to be disconnected from the syringe barrel for recycling after the service of the hypodermic syringe and after the needle assembly has been received inside the syringe barrel. According to the present invention, the safety hypodermis syringe is comprised of a barrel, needle assembly, and a plunger assembly. The needle assembly has a coupling means at the rear side of the needle hub thereof. The plunger assembly comprises a stopper holder holding a stopper, and a plunger connected to the rear side of the stopper holder. The stopper holder has front coupling means coupled to the coupling means of the needle assembly, and a rear coupling means. The plunger has a coupling means at the front side thereof coupled to the rear coupling means of the stopper holder for enabling the needle assembly and the stopper holder with the stopper to be moved backwards and received inside the barrel upon back stroke of the plunger after the service of the syringe to prevent possible contamination. After back stroke of the plunger, the plunger can be disconnected from the stopper holder and removed out of the barrel for recycling.

DETAILED DESCRIPTION OF THE PREFERRED EMBODIMENT

Figure 1:
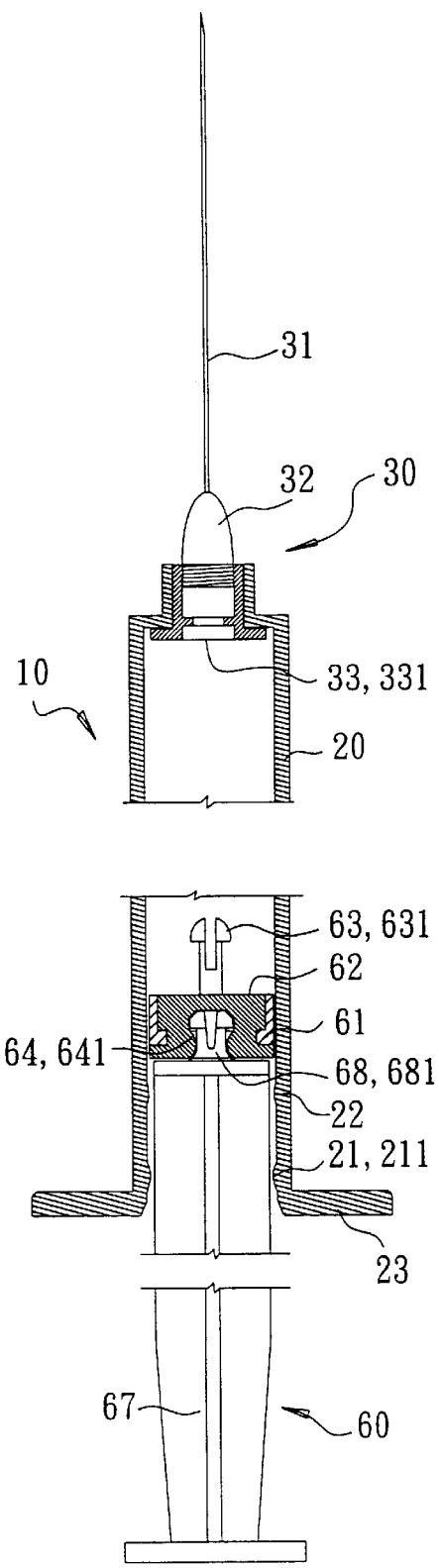
FIG. 1 is a sectional view of a safety hypodermic syringe according the present invention.

Referring to FIG. 1, a safety hypodermic syringe 10 is shown comprised of a barrel 20, a needle assembly 30, and a plunger assembly 60.

The needle assembly 30 comprises a needle cannula 31, a needle hub 32 holding the needle cannula 31, and female coupling means 33 provided at the rear side of the needle hub 32 opposite to the needle cannula 31. According to the present preferred embodiment, the female coupling means 33 is a coupling hole 331.

The barrel 20 is a hollow cylindrical member comprising a finger flange 23 integral with the rear end thereof, a first inside protrusion 21, and a second inside protrusion. The arrangement of the first inside protrusion 21 and the second inside protrusion 22 will be described in FIG. 5.

Figure 2:
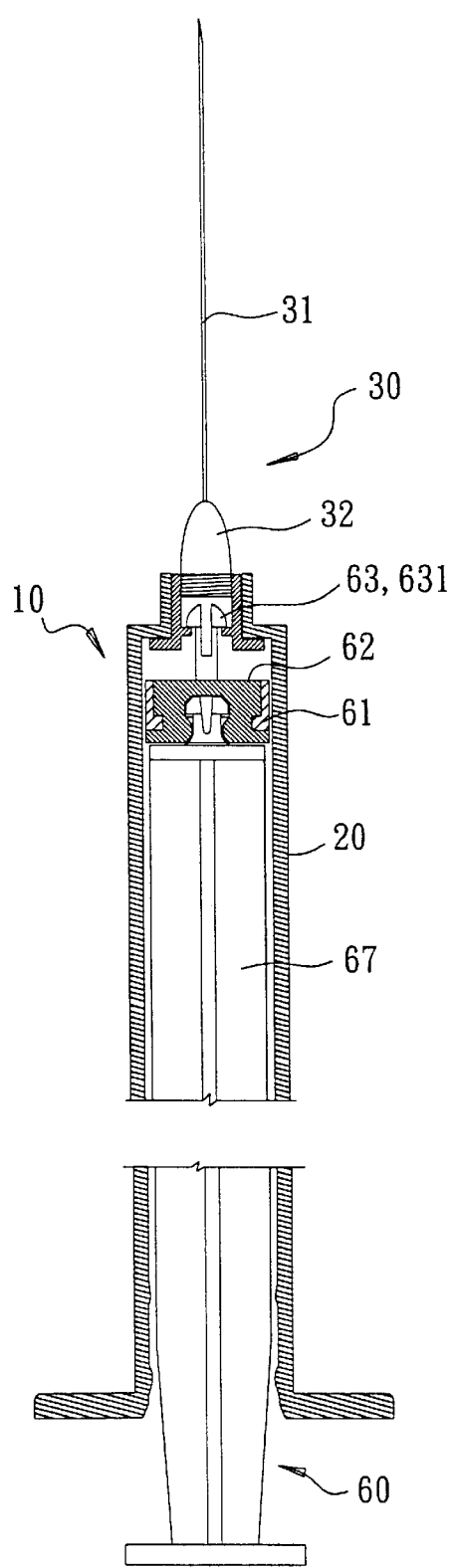
FIG. 2 is a sectional view of the present invention showing the plunger moved to the front limit position after injection.
Figure 3:
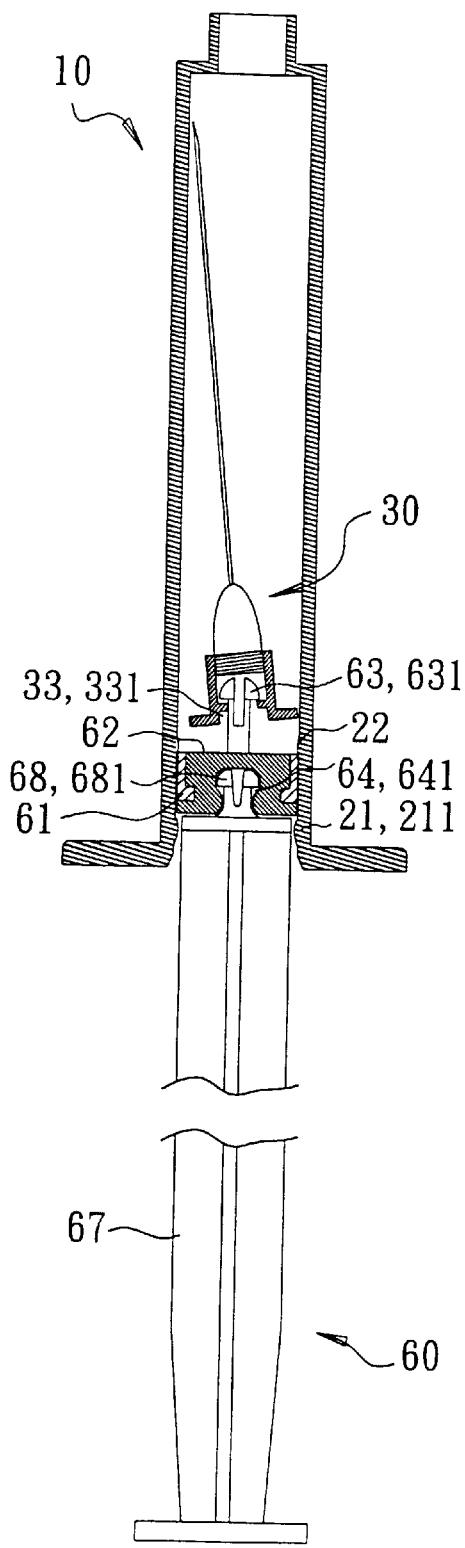
FIG. 3 is another sectional view of the present invention showing the plunger moved to the rear limit position in the barrel and the needle assembly received inside the barrel.

The plunger assembly 60 comprises a stopper 61, a stopper holder 62, male coupling means 63, and a plunger 67. The stopper 61 is covered on the periphery of the stopper holder 62, and fits the inner diameter of the barrel 20. The male coupling means 63 extends forwardly from the center of the front side of the stopper holder 62, and adapted for engaging into the coupling means 33 (coupling hole 331) of the needle assembly 30. According to the present preferred embodiment, the male coupling means 63 is a split coupling bolt 631. After injection, the plunger 67 is pushed to the front limit position, forcing the split bolt 631 into engagement with the coupling hole 331 (see FIG. 2), and therefore the needle assembly 30 is moved backwards and received inside the barrel 20 when the user pulls back the plunger 67 (see FIG. 3). This safety design is of the known art and not within the scope of the claims of the present invention. The coupling structure between the plunger assembly 60 and the needle assembly 30 (the female coupling means 33 and the male coupling means 63) may be variously embodied.

The stopper holder 62 comprises female coupling means 64, for example, a coupling hole 641 at the back side thereof. The plunger 67 comprises male coupling means 68, for example, a split coupling bolt 681. The split coupling bolt 681 is fastened to the coupling hole 641, keeping the plunger holder 62 and the plunger 67 connected in a line.

Figure 4:
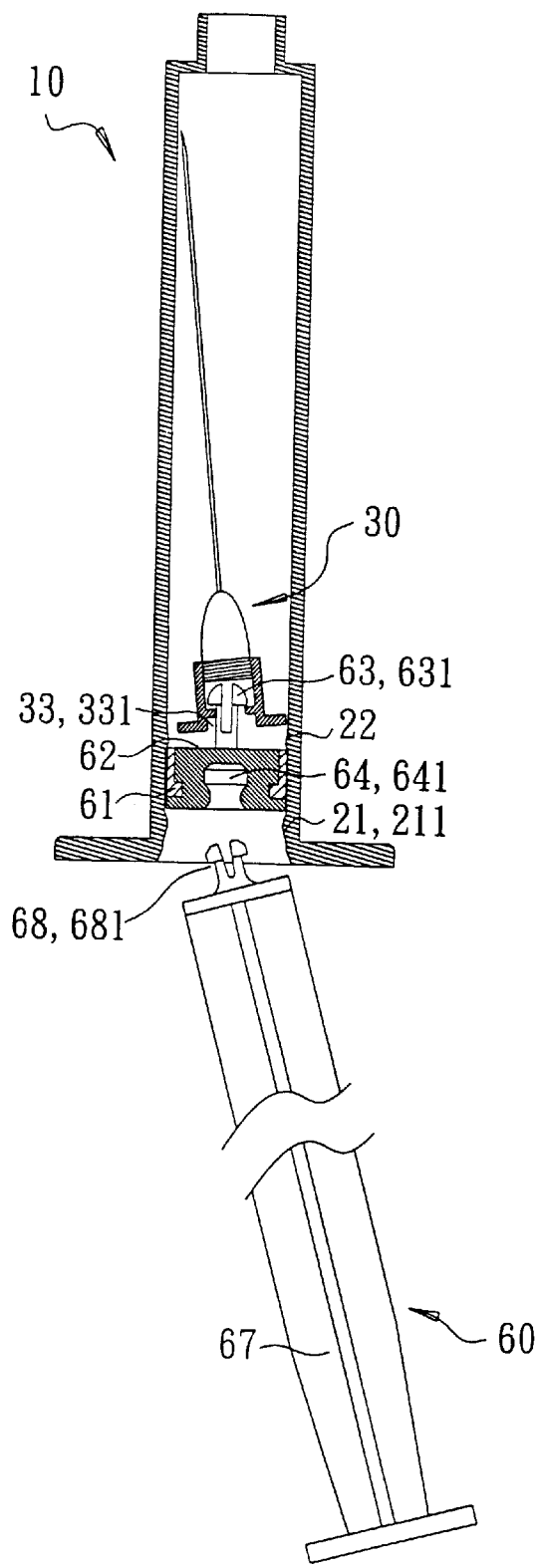
FIG. 4 is still another sectional view of the present invention showing the plunger disconnected from the stopper.

Referring to FIG. 4, after the plunger assembly 60 has been pulled to the back side to receive the needle assembly 30 inside the barrel 20, the user can turn the plunger 67 sideways to disconnect the plunger 67 from the stopper holder 62, thus the plunger 67 can be recycled, or separately disposed of.

When pulling the plunger assembly 60 to the back side of the barrel 20, the stopper 61 and the stopper holder 62 will be stopped at the first inside protrusion 21, and the user must employ much effort to pull the whole plunger assembly 60 out of the barrel 20.

Figure 5:
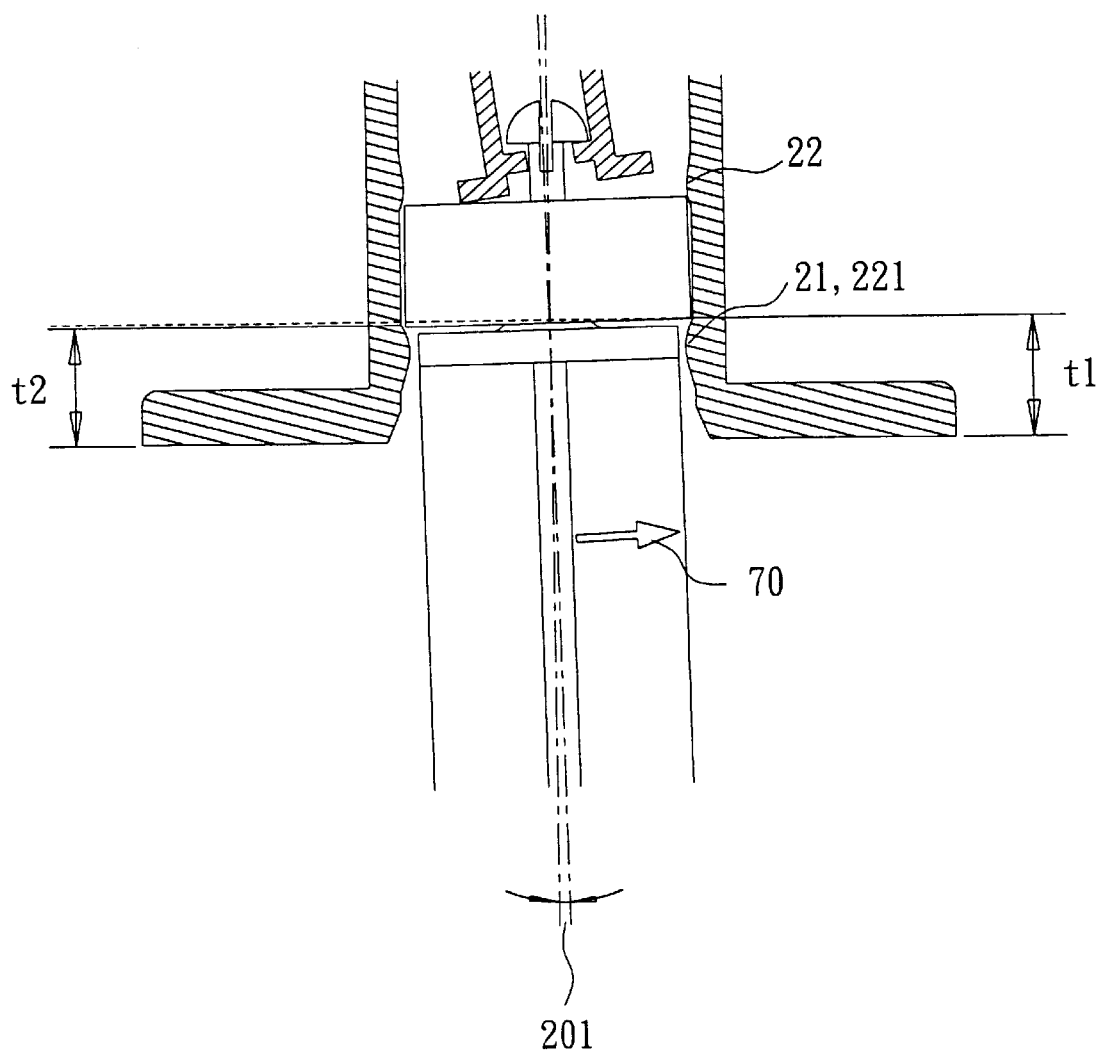
FIG. 5 is a sectional view on an enlarged scale of a part of the present invention.

Referring to FIG. 5, the first inside protrusion 21 is an inside annular flange 211 rose around the inside wall of the barrel 20 near the finger flange 23. The plane defined by the inside annular flange 211 is not perfectly perpendicular to the axis 201 of the barrel 20 (for example, t1>t2). When the user pulls the plunger assembly 60 to the back side of the barrel 20, the plunger 67 is forced to tilt in one direction, producing a side force 70, and at the same time the plunger assembly 30 is tilted in the barrel 20. Therefore, the first inside protrusion 21 effectively prevents the whole plunger assembly 60 from being pulled out of the barrel 20.

Further, the second inside protrusion 22 is designed for enabling the stopper 61 with the stopper holder 62 to be positioned in between the first inside protrusion 21 and the second inside protrusion 22, preventing the stopper 61 with the stopper holder 62 from being pushed forwards to the front side of the barrel 20 after back stroke of the plunger 67.

While only one embodiment of the present invention has been shown and described, it will be understood that various modifications and changes could be made thereunto without departing from the spirit and scope of the invention disclosed.

What the invention claimed is:

1. A safety hypodermic syringe comprising:

a needle assembly, said needle assembly comprising a needle cannula, a hollow needle hub having a front side holding said needle cannula and a rear side providing-with coupling means;

a barrel defining a cylindrical inside receiving chamber, said barrel comprising a finger flange at a rear side thereof; and a plunger assembly, said plunger assembly comprising a stopper holder having a front side and a rear side, a stopper covered on the periphery of said stopper holder, and a plunger connected to the rear side of said stopper holder, said stopper holder comprising first coupling means disposed at the front side thereof and adapted to engage the coupling means of said needle hub for enabling said needle assembly to be pulled backwards with said plunger assembly and received inside said barrel, and a second coupling means disposed at the rear side thereof, said plunger comprises coupling means disposed at a front side thereof and coupled to the second coupling means of said stopper holder for enabling said stopper holder, said stopper and said needle assembly to be moved with said plunger upon back stroke of said plunger and said plunger to be disconnected from said stopper holder and removed from said barrel after said needle assembly has been received inside said barrel.

2. The safety hypodermic syringe of claim 1 wherein the second coupling means of said stopper holder is a coupling hole, and the coupling means of said plunger is a split coupling bolt.

3. The safety hypodermic syringe of claim 1 wherein said barrel comprises a first inside protrusion raised from an inside wall thereof near said finger flange and adapted to stop said stopper holder and said stopper inside said barrel.

4. The safety hypodermic syringe of claim 3 wherein said first inside protrusion is an inside annular flange.

5. The safety hypodermic syringe of claim 4 wherein said inside annular flange defines a plane that is not perpendicular to the axis of said barrel.

6. The safety hypodermic syringe of claim 3 wherein said barrel further comprises a second inside protrusion raised around the inside wall thereof in front of said first inside protrusion and adapted for enabling said stopper and said stopper holder to be positioned in between said first inside protrusion and said second inside protrusion after back stroke of said plunger.

* * * * *